United States Patent [19]
Henry

[11] Patent Number: 5,137,022
[45] Date of Patent: Aug. 11, 1992

[54] SYNCHRONOUS TELEMETRY SYSTEM AND METHOD FOR AN IMPLANTABLE MEDICAL DEVICE

[75] Inventor: Donald A. Henry, Greensburg, Pa.

[73] Assignee: Cook Pacemaker Corporation, Leechburg, Pa.

[21] Appl. No.: 553,435

[22] Filed: Jul. 13, 1990

[51] Int. Cl.⁵ .............................................. A61N 1/37
[52] U.S. Cl. ................................ 128/419 PT; 128/903
[58] Field of Search ................ 128/419 PT, 697, 903, 128/904

[56] References Cited

U.S. PATENT DOCUMENTS

| | | | |
|---|---|---|---|
| 4,026,305 | 5/1977 | Brownlee et al. | 128/419 PT |
| 4,223,679 | 9/1980 | Schulman et al. | 128/419 PT |
| 4,237,895 | 12/1980 | Johnson | 128/419 PG |
| 4,281,664 | 8/1981 | Duggan | 128/696 |
| 4,374,382 | 2/1983 | Markowitz | 128/419 OP |
| 4,409,984 | 10/1983 | Dick | 128/696 |
| 4,522,208 | 6/1985 | Buffet | 128/419 PT |
| 4,543,953 | 10/1985 | Slocum et al. | 128/419 PT |
| 4,550,370 | 10/1985 | Baker | 128/419 P |
| 4,556,063 | 12/1985 | Thompson et al. | 128/419 PT |
| 4,681,111 | 7/1987 | Silvian | 128/419 PT |
| 4,686,990 | 8/1987 | Moberg | 128/419 PT |
| 4,741,340 | 5/1988 | Batina et al. | 128/419 PT |
| 4,757,816 | 7/1988 | Ryan et al. | 128/419 PT |
| 4,791,936 | 12/1988 | Snell et al. | 128/697 |

OTHER PUBLICATIONS

Kennedy, G. "Electronic Communication Systems," 2d ed., 575-581 (1977).
Schwartz, M. "Information Transmission, Modulation, and Noise," 2d ed., 176-183 (1970).
Marko, "Aerospace Medicine" vol. 32, pp. 1019-1022, Nov. 1961.

*Primary Examiner*—William E. Kamm
*Attorney, Agent, or Firm*—Woodard, Emhardt, Naughton, Moriarty & McNett

[57] ABSTRACT

A synchronous telemetry system and method for multiplexed telemetry of analog and digital information from a pacemaker or other implantable medical device. Telemetry sync pulses are generated at a 1 kHz rate, and pulse-position modulation is employed for generating an analog data pulse and a digital data pulse relative to the same sync pulse and displaced therefrom by different intervals respectively corresponding to the instantaneous value of an analog input signal and the instantaneous state of a digital input signal. In addition to multiplexing of analog and digital information in a composite bit, multiplexing is provided for dual-channel analog operation.

21 Claims, 10 Drawing Sheets

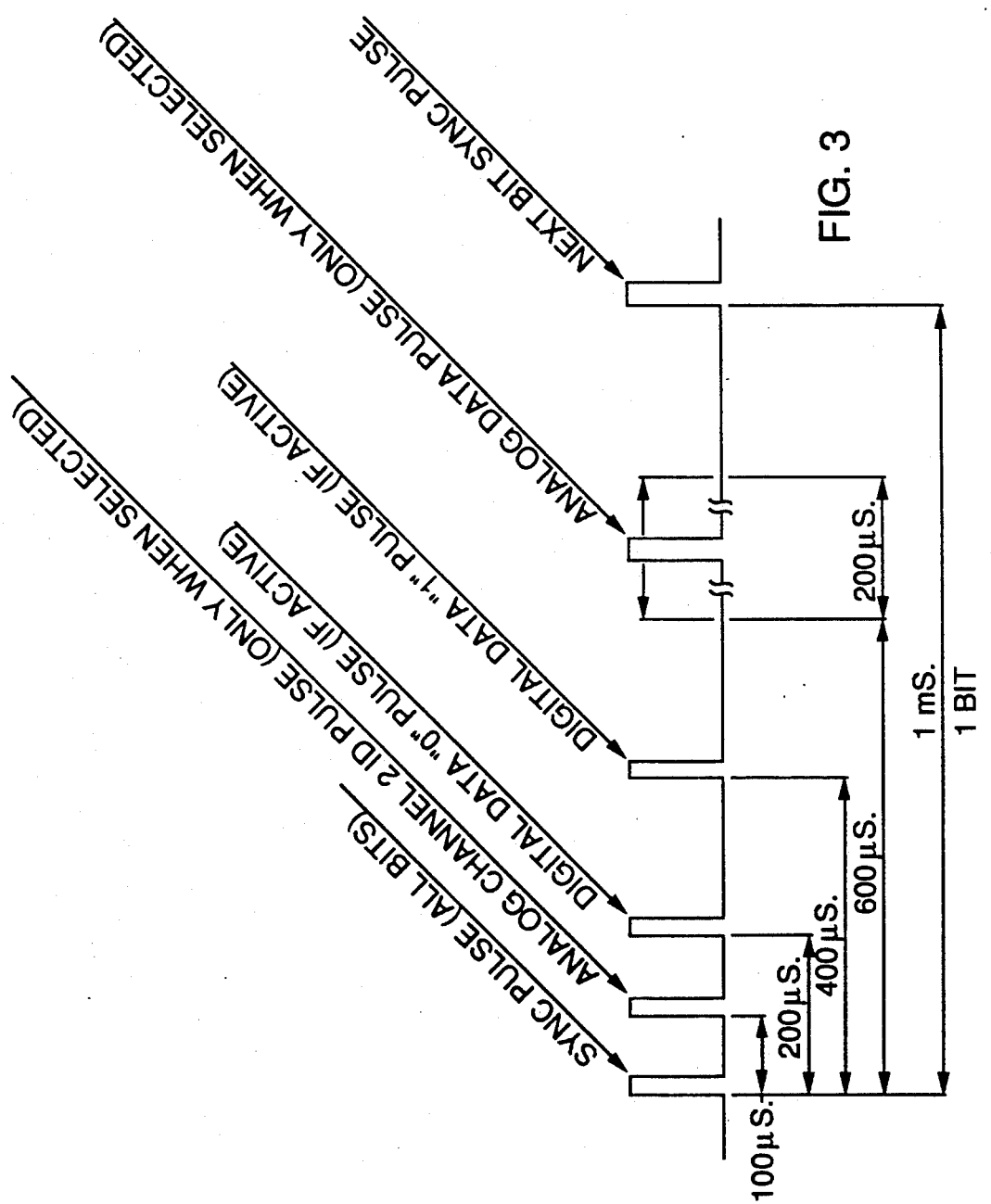

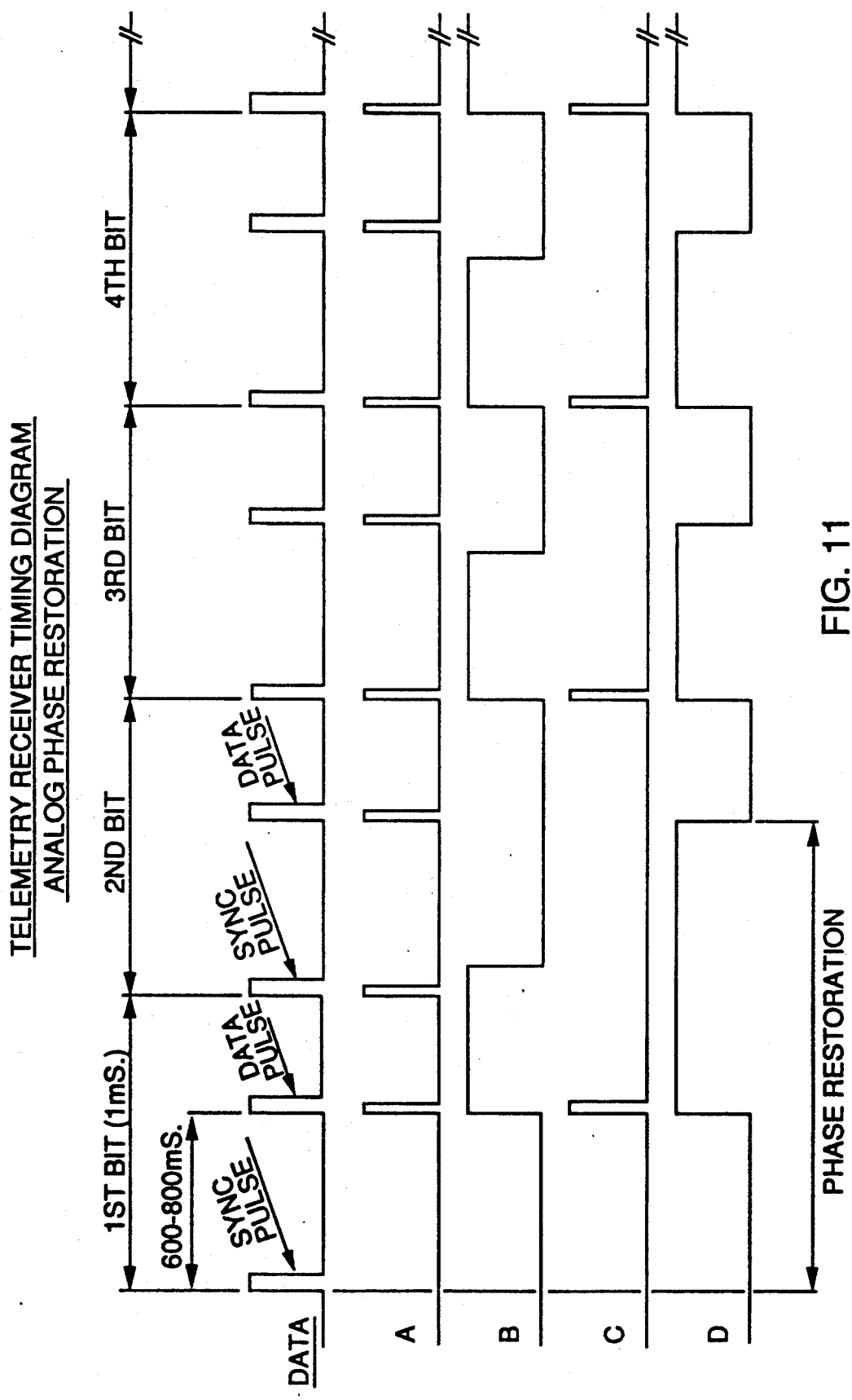

SYNCHRONOUS TELEMETRY SYSTEM AND METHOD FOR AN IMPLANTABLE MEDICAL DEVICE

BACKGROUND OF THE INVENTION

The invention relates to telemetry systems for use in cardial pacemakers and other implantable medical devices, and more particularly to such telemetry systems employing pulse modulation.

Modern pacemakers conventionally employ some form of communications link for transmission and reception of information when implanted in the body of a patient. External programming devices are routinely used for remotely programming operating mode and other parameters affecting pacemaker operation, such as stimulation pulse rate, escape interval, refractory period, pulse width, pulse amplitude, and sensitivity. In addition, pacemakers commonly have the capability of transmitting status information as well as biological information via telemetry. Actual settings of operating mode and other programmed parameters may be ascertained in this manner, as may the condition of the pacemaker battery. Electrical activity within the heart, temperature, and other physiological parameters sensed by pacemakers have also been externally monitored via telemetry.

Examples of various telemetry methods and forms of modulation which have been employed for communicating non-invasively through the skin may be found in the following U.S. Pat. Nos.:

| U.S. Pat. No. | Inventor | Issue Date | Modulation* |
|---|---|---|---|
| 4,026,305 | Brownlee et al. | May 31, 1977 | PIM |
| 4,223,679 | Schulman et al. | Sep. 23, 1980 | FM/FM, FM/AM |
| 4,237,895 | Johnson | Dec. 9, 1980 | PIM, PWM |
| 4,281,664 | Duggan | Aug. 4, 1981 | FM, FSK |
| 4,409,984 | Dick | Oct. 18, 1983 | FM |
| 4,522,208 | Buffet | Jun. 11, 1985 | PPM |
| 4,543,953 | Slocum et al. | Oct. 1, 1985 | PM, PSK |
| 4,550,370 | Baker | Oct. 29, 1985 | PIM |
| 4,556,063 | Thompson et al. | Dec. 3, 1985 | PIM |
| 4,681,111 | Silvian | Jul. 21, 1987 | FM, PSK, PWM, PPM, FSK |
| 4,686,990 | Moberg | Aug. 18, 1987 | PPM |
| 4,741,340 | Batina et al. | May 3, 1988 | PWM |
| 4,757,816 | Ryan et al. | Jul. 9, 1988 | PIM |
| 4,791,936 | Snell et al. | Dec. 20, 1988 | FM, PAM/PWM, PSK |

*AM = Amplitude Modulation
FM = Frequency Modulation
FSK = Frequency Shift Keying
PM = Phase Modulation
PAM = Pulse Amplitude Modulation
PIM = Pulse Interval Modulation
PPM = Pulse Position Modulation
PSK = Phase Shift Keying
PWM = Pulse Width Modulation Among those patents describing some form of pulse modulation, the patent to Moberg discloses a pacemaker battery test circuit which positions a marking pulse at a chronological position between successive stimulation pulses which depends on the charge status of the battery. Generation of the marking pulses is dependent upon stimulation pulses generated by the pacemaker. The system apparently allows for transmission of only one bit of information during any given cardiac cycle, and, as such, is extremely limited in terms of data rate.

The Buffet patent discloses a digital telemetry system intended to provide the capability of checking the actual settings of a large number of programmable parameters having a large range of possible settings, i.e., 16 possible values for any parameter in the disclosed embodiment. A parameter value is assigned a time $\Delta T$ which is a fraction of the pacing period T (the cardiac cycle), and then two successive pacing intervals with a combined duration of 2T are altered by shortening one and lengthening the other by the amount $\Delta T$. The parameter value is identified externally by comparing the relative lengths of the two altered intervals. Telemetry is performed only with the pacemaker operating in asynchronous mode at a predetermined pacing rate. The actual data rate is quite low in that two full cardiac cycles, e.g., two seconds at 60 pulses per minute, are required for transmission of a single digital value. Such a data rate is unacceptably low for many applications of telemetry of data from an implantable device.

Thompson et al. discloses an asynchronous telemetry system for pacemakers in which the interval between transmitted pulses corresponds to the amplitude of an analog signal. As the analog voltage varies, the pulse interval, controlled by a variable-frequency oscillator, varies in a range between 600–1000 microseconds, as illustrated by the waveform of FIG. 3 of that patent. Oscillator-triggered bursts of RF energy from a tank circuit are coupled to an external receiver. The oscillator is free-running.

Another asynchronous telemetry system operating with a free-running oscillator is disclosed in the Brownlee et al. patent cited above, which mentions pulse-interval modulation primarily for telemetry of battery voltage, and also mentions further modulation of the carrier frequency at higher modulation rates for telemetry of refractory delay time and pacing pulse amplitude and/or width. Similarly, in the patent to Johnson, the interval between pacer pulses is indicated as a measure of the status of the pacer battery. Ryan et al. discloses an asynchronous telemetry system in which the intracardiac electrogram is applied as the control signal to a voltage-controlled pulse generator.

Several of the above-referenced patents, such as Silvian, Duggan, Baker, and Thompson et al., describe systems capable of selective transmission of either analog or digital information from a pacemaker. Thompson et al. also mentions a time division multiplexing scheme for sequential transfer of more than one channel of analog data, such as atrial and ventricular electrograms from a dual-chamber pacemaker. The system of Thompson et al. shifts a nominal oscillator frequency to accommodate a second analog channel, and thereby produces an additional range of pulse intervals which need to be measured in the external receiver to demodulate the information on the second channel. The system appears to complete the transmission of digital data before initiating transmission of analog data.

In spite of the existence of numerous techniques for telemetry of analog and digital data from implantable medical devices, there remains a need for a better overall solution to the various problems faced in the design of such telemetry systems, such as the need for extremely low power consumption, operation from a low-voltage source, minimum circuit parts count, circuit reproducibility, compatibility with active devices available for such applications, and acceptable digital data rates and/or practical analog channel bandwidths.

SUMMARY OF THE INVENTION

The present invention provides an improved telemetry system and method in which, in a first embodiment especially suited for a pacemaker, a plurality of telemetry sync pulses are generated between consecutive pacing pulses, and pulse-position modulation is employed to displace an analog data pulse from one of the sync pulses by an interval corresponding to the instantaneous value of an analog input signal. The analog data pulse is transmitted along with the associated sync pulse to an external device.

According to another aspect of the invention, a system and method are provided for synchronous multiplexed telemetry of analog and digital information from an implantable medical device. Pulse-position modulation is employed for generating an analog data pulse and a digital data pulse relative to the same sync pulse in a plurality of telemetry sync pulses. The analog data pulse and digital data pulse are displaced from the same sync pulse by different intervals respectively corresponding to the instantaneous value of an analog input signal and the instantaneous state of a digital input signal. The analog and digital data pulses are transmitted along with the sync pulses to an external device. The implantable medical device may be a cardiac pacemaker, which term is meant to include devices for controlled stimulation of a natural heart as well as pacing and control units for other devices such as artificial hearts and ventricular assist devices, or may be an implantable defibrillator or cardioverter, an implantable drug-dispensing device, or other implantable device such as for therapy or sensing with respect to the brain, spinal cord, muscles, bones, nerves, or other body organs or tissue.

A general object of the present invention is to provide an improved system and method for telemetry of data from an implantable medical device.

Another object is to better accommodate the electrical and physical constraints imposed on implantable devices.

Other objects and advantages of the present invention will become apparent upon reading the following detailed description of the preferred embodiment in conjunction with the accompanying drawings.

BRIEF DESCRIPTION OF THE DRAWINGS

FIG. 3 is a timing diagram which illustrates the bit encoding in a composite analog and digital telemetry bit according to the preferred embodiment of the present invention.

FIG. 11 is a timing diagram for the telemetry receiver of FIGS. 7-10.

DESCRIPTION OF THE PREFERRED EMBODIMENT

Figure 1:
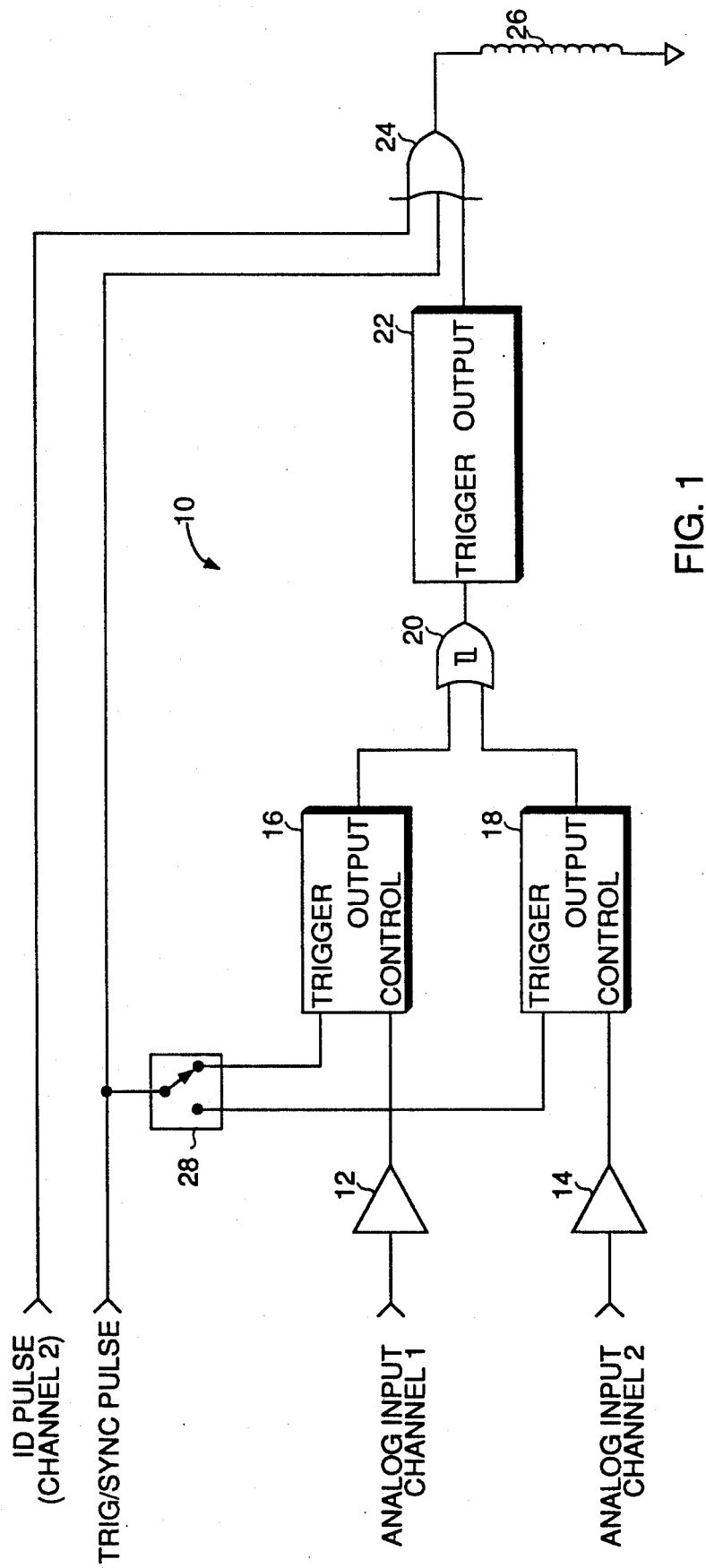
FIG. 1 is a simplified block diagram of a synchronous dual-channel analog telemetry pulse generator according to the preferred embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
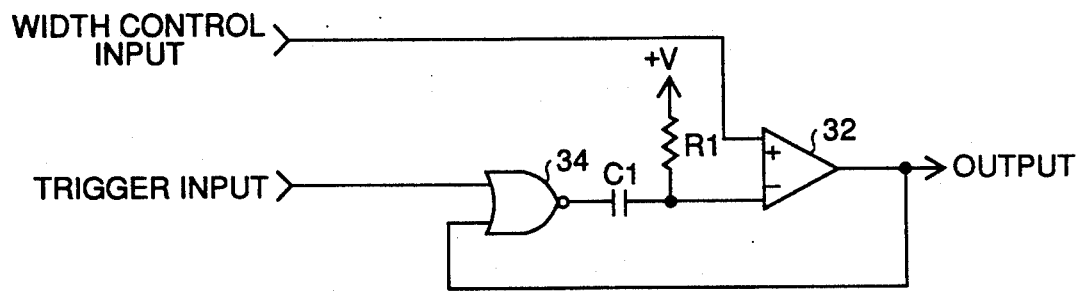
FIG. 2 is an electrical schematic of a voltage-controlled monostable multivibrator of the type shown in FIG. 1.

A dual-channel analog telemetry pulse generator according to the present invention is illustrated in FIG. 1 and denoted generally by reference numeral 10. The generator includes separate analog input amplifiers 12 and 14 for analog processing, including scaling, of signals on analog input channels 1 and 2, respectively. The outputs of amplifiers 12 or 14 are coupled to the control inputs of voltage-controlled monostable multivibrators 16 and 18, each of which is configured as shown in FIG. 2. As will be appreciated by those skilled in the art, each voltage-controlled monostable, or one-shot, is triggered by a high ("1") logic level on the trigger input, connected to one input of NOR gate 34, whereupon the output of comparator 32 goes high and remains high until capacitor C1 charges, through resistor R1, to a voltage exceeding the instantaneous voltage of the analog input signal which is supplied to the width control input. The value of R1 should be kept as high as possible so as to minimize current consumption. Presently preferred values of R1 and C1 are 8.2 MΩ and 220 pF, respectively.

Figure 5:
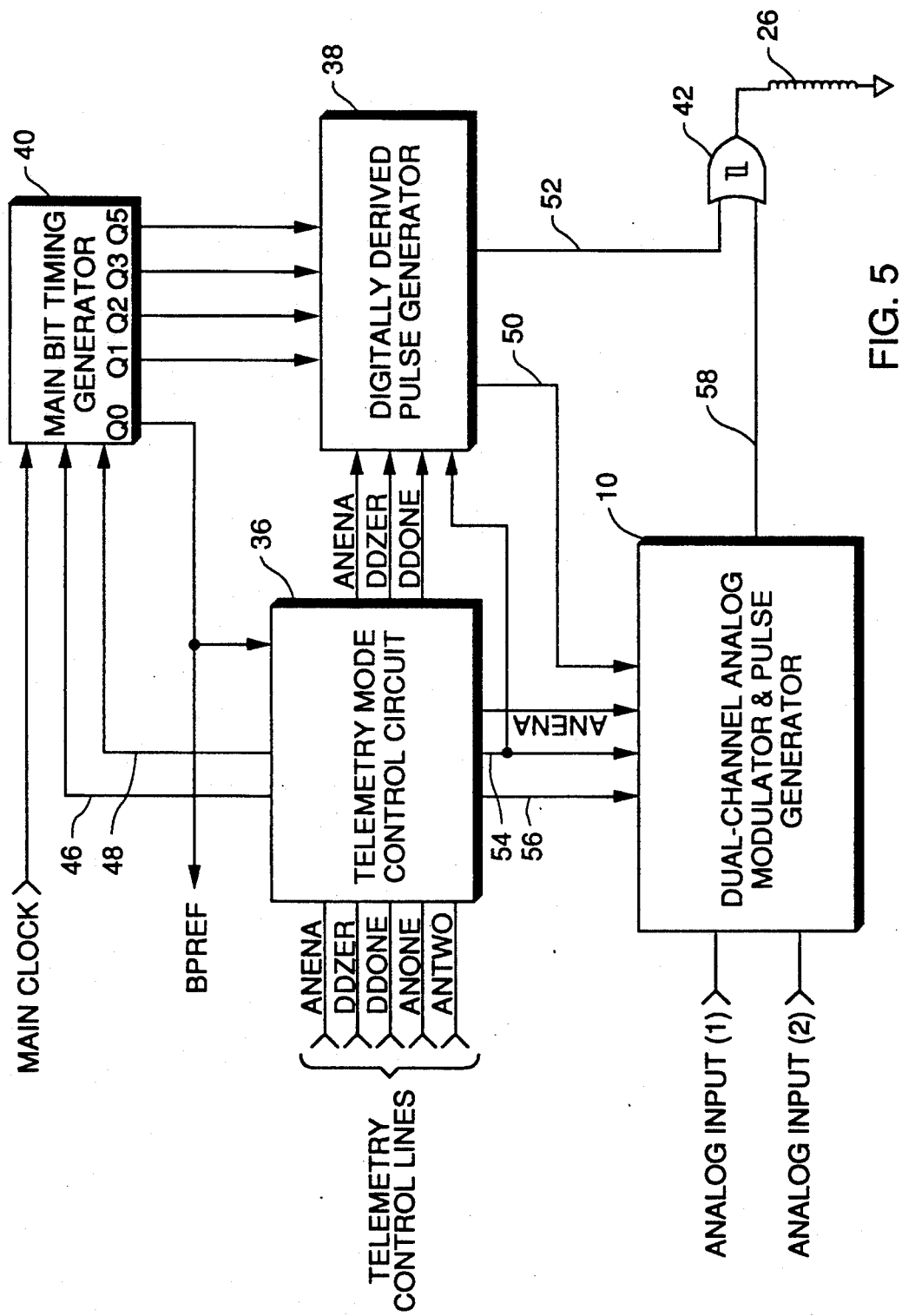
FIG. 5 is a block diagram of a synchronous telemetry system for multiplexed telemetry of analog and digital information according to the preferred embodiment of the present invention.

Voltage-controlled monostable (VCM) 16 is preferably triggered at a 1 kHz rate, i.e., once every millisecond, in single-channel mode, as will be described, and monostables 16 and 18 are alternately triggered during dual-channel operation, via channel multiplexing circuit (MUX) 28, which is toggled every millisecond, resulting in an individual analog channel sample rate of 500 Hz. The R1-C1 time constant of each monostable and the scaling components in input amplifiers 12 and 14 are selected such that the duration of each output pulse of each monostable varies linearly in a 200-microsecond (μS) range as a function of analog input voltage for an input range of ±20 millivolts (mV) supplied to the associated channel input. The linear range preferably has a minimum time interval of 600 μS, corresponding to an input voltage of −20 mV, and a maximum time interval of 800 μS, corresponding to an input voltage of +20 mV. The conclusion of each monostable output pulse triggers a fixed-length monostable 22, to which monostable multivibrators 16 and 18 are coupled through an OR gate 20. The output of monostable 22 drives a coupling coil 26 through an OR gate 24 which is depicted with three inputs to illustrate its function of passing all pulses associated with analog data telemetry. As will be explained later, the ID pulse and trigger/sync (TRIG/SYNC) pulse are preferably supplied on the same line to a two-input OR gate, as shown in FIG. 5 (gate 42). FIG. 3 illustrates the relative timing of the sync pulse which triggers a voltage-controlled monostable and the resulting analog data pulse, as well as the relative timing of other pulses combined therewith to form a composite analog and digital telemetry data bit, as will be further described herein.

The width of each pulse conveys no information, and, accordingly, all pulses are preferably very narrow, on the order of 25 μS or less in duration, so as to minimize power consumption. All information to be telemetered is contained in the time displacement of a pulse from its associated sync pulse, and most preferably in the time displacement between the leading edges of the pulses. For example, the time length between the leading edge of a sync pulse and the leading edge of an associated analog data pulse corresponds to the instantaneous voltage of the telemetered analog signal. An external receiver measures the time between the sync and data pulses and recreates the original analog (modulating) signal. Circuitry is incorporated into the data receiver which will automatically distinguish between the sync and data pulses so as to preserve analog signal phase, as will be described later in detail.

For channel identification purposes at the receiving end, an ID pulse is transmitted 100 microseconds after the bit sync pulse when analog channel 2 is selected, to indicate that the current analog data bit corresponds to channel 2, as illustrated in FIG. 3. The ID pulse is not generated when channel 1 is selected, and only one of the two digital data pulses shown in FIG. 3 is generated during any one bit of digital data telemetry.

Single-channel operation may be accomplished, if desired, simply by maintaining multiplexer 28 in the position corresponding to channel 1. Alternatively, a simplified circuit may be provided in which the trigger/sync pulse is supplied directly to the trigger input of monostable 16 instead of through a multiplexer, and in which the output of monostable 16 is connected directly to the trigger input of monostable 22 instead of through an OR gate. A further reduction in parts count in the simplified circuit results from the elimination of amplifier 14 and monostable 18.

Figure 4A:
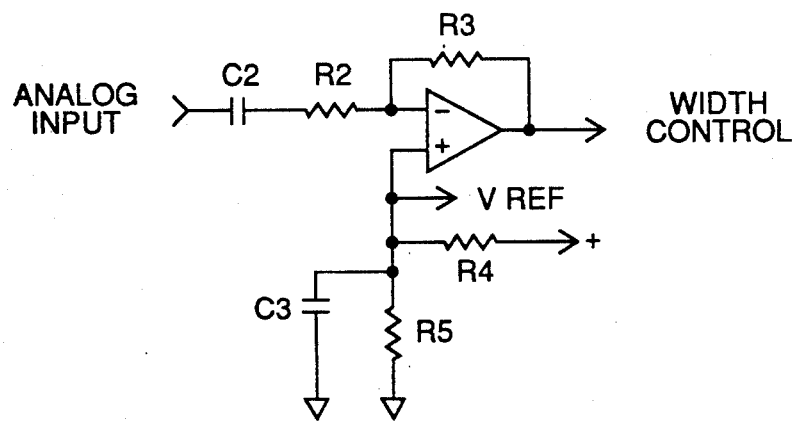
FIG. 4A is an electrical schematic of an analog input amplifier of the type shown in FIG. 1.

Input amplifiers 12 and 14 are both configured as shown in FIG. 4A, with separate but identical input and feedback impedances C2, R2 and R3, and with a common impedance network consisting of resistors R4 and R5 and capacitor C3 connected as shown. Amplifiers 12 and 14 are preferably op amp circuits each using one of the two op amps in a 4575 dual/dual amplifier-comparator in the 4000 series of CMOS devices. The two comparators in the 4575 are preferably used for the comparators 32 in VCMs 16 and 18. The presently preferred values for the passive components in the input amplifiers are as follows:

| Component | Value |
|---|---|
| R2, R5 | 1 MΩ |
| R3 | 3.3 MΩ |
| R4 | 1.8 MΩ |
| C2 | 0.1 μF |
| C3 | 1 μF |

Figure 4B:
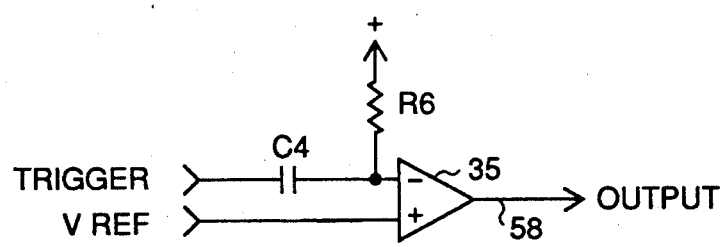
FIG. 4B is an electrical schematic of a fixed-length monostable multivibrator of the type shown in FIG. 1.

The reference voltage (VREF) shown in FIG. 4A is supplied to the noninverting input of a comparator 35 in fixed one-shot 22, the schematic of which is shown in FIG. 4B. As will be appreciated by those skilled in the art, one-shot 22 is triggered by the trailing edge of a VCM output pulse supplied to its trigger input, whereupon its output goes high and remains high until capacitor C4 charges, through resistor R6, to a voltage exceeding VREF. Presently preferred values of R6 and C4 are 200 KΩ and 220 pF, respectively.

Referring now to FIG. 5, dual-channel analog modulator and pulse generator 10 shown in FIG. 1 is preferably part of a combined analog and digital synchronous telemetry system which includes a telemetry mode control circuit 36 coupled to analog modulator 10 and further includes a digitally derived pulse generator 38, main bit timing generator 40, and OR gate 42 connected as shown in the drawing. 4000 series CMOS devices are used for all active components in the transmitter circuit of FIG. 5. The telemetry system may be contained within any one of the implantable medical devices previously described, but the preferred embodiment will be described in the context of a programmable pacemaker having a pulse generator and a microprocessor for monitoring and control of pacing functions. The pacemaker is powered by a battery in conventional fashion, and the battery also supplies power to the telemetry system.

Telemetry system operation is initiated by a combination of mode control signals generated by the pacemaker microprocessor and supplied to the telemetry system on the telemetry control lines shown in FIG. 5 and identified as follows:

ANENA = Analog enable
ANONE = Analog channel 1, enable only
ANTWO = Analog channel 2, enable only
DDZER = Digital data zero enable
DDONE = Digital data one enable A 6502 microprocessor, among others, is suitable for generation of these control signals as required in the preferred embodiment of the telemetry system. Under control of these control signals, the telemetry system is capable of either single-channel or dual-channel (multiplexed) analog data telemetry, and/or single-channel digital data telemetry.

Digital data to be transmitted from the pacemaker are first supplied to telemetry mode control circuit 36 on the DDZER and DDONE telemetry control lines, the states of which must be complementary for any single telemetry bit. In response, pulse generator 38 generates a digital data pulse at one or the other of two positions in the composite analog and digital bit as shown in FIG. 3, digital data "0" being represented by a pulse beginning 200 μS after the leading edge of the sync pulse, and digital data "1" being represented by a pulse beginning 400 μS after the leading edge of the sync pulse. Insertion of the digital data pulse is accomplished via line 52 and OR gate 42, which receives the analog data pulse for the composite telemetry bit via line 58 from analog modulator 10. The ID pulse for channel 2 is generated by pulse generator 38 as a function of the ANENA control signal and the state of a channel selection flip-flop to which it is connected via line 54. Pulse generator 38 also outputs each sync pulse on line 52.

The timing of all telemetry pulses is controlled by timing signals supplied on the Q1, Q2, Q3 and Q5 outputs of main bit timing generator 40 which in turn is controlled by the main clock of the pacemaker, typically in the range of 20 to 50 kHz and preferably 40 kHz. The sync pulses, ID pulses and digital data pulses are all digitally derived from the main clock and are preferably 25 μS in duration. The analog data pulses are of approximately the same duration, although their pulse width is controlled by one-shot 22 (FIG. 1) instead of the main clock.

Timing generator 40 is initialized by reset signals supplied on lines 46 and 48 from mode control circuit 36, and, at the beginning of each bit cycle, supplies a pulse from output Q0 to the microprocessor in the pacemaker and also to mode control circuit 36 as a bit position reference (BPREF).

As alluded to previously, analog data pulses are confined to a "window" extending from 600 μS to 800 μS after their respective sync pulses. The last half of each bit is dedicated to analog data. That is, from 500 μS after a sync pulse until the next bit sync pulse, no other pulses are transmitted except an analog data pulse. Proper analog signal phase can be maintained by reserving the last half of the bit in this manner.

Transfer of digital information occurs, if at all, in the first half of a data bit. Thus, as described above and as illustrated in FIG. 3, the system can selectively telemeter analog or digital information or telemeter both analog and digital information within a single bit. The analog channel-identifying pulse occurs, if at all, during the first half of the bit, and is kept totally separate from digital data pulses, whereby no digital information is lost during simultaneous telemetry of dual-channel analog data and digital data.

Figure 6:
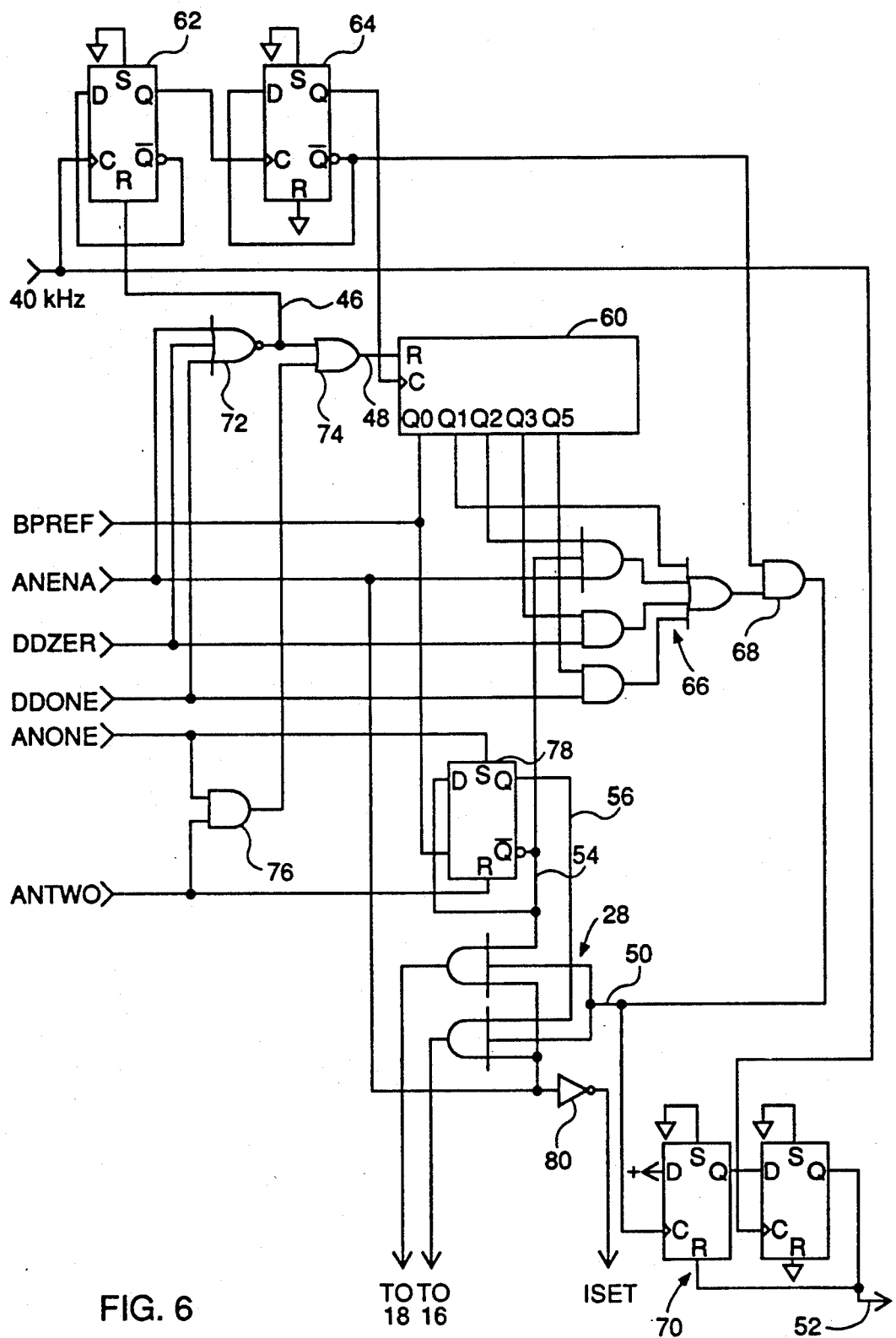
FIG. 6 is an electrical schematic of the timing generator, mode control circuit and digitally derived pulse generator shown in FIG. 5.

Referring now to FIG. 6, the circuitry contained within the various blocks in FIG. 5 is shown in further detail. Counter 60 and a frequency divider using D flip-flops 62 and 64, along with their associated interconnection lines, together form main bit timing generator 40. Counter 60 is preferably a 4017 decade counter. Similarly, gates 72, 74 and 76 and D flip-flop 78, along with their associated interconnection lines, together form mode control circuit 36. Digitally derived pulse generator 38 consists of a combinational logic circuit 66 including three AND gates connected, as shown, to respective outputs Q2, Q3 and Q5 of counter 60 and a four-input OR gate which has one input connected to output Q1 of counter 60, as well as an AND gate 68 and a digital one-shot 70 designed with a pair of D flip-flops connected as shown in the drawing.

FIG. 6 also shows MUX 28 of FIG. 1 in further detail, as well as an inverter 80 the input of which is connected to the ANENA control line. The output lines to 16 and to 18 are connected to the trigger inputs of VCM 16 and VCM 18, respectively. The output of the inverter is connected to the ISET inputs of the op amps and comparators in analog modulator 10 through current-setting resistors, preferably through an individual 10 MΩ resistor for each such ISET input, in order to reduce the drain on the pacemaker battery during operation. When analog telemetry is not desired, the drain on the battery can be minimized by disabling the op amps and comparators in the analog modulator; this is accomplished by setting the ANENA line low and thereby supplying a high output state at the output of inverter 80.

The pacemaker commands the telemetry system to operate in response to a telemetry request signal received via communications coupling coil 26 and processed through programming receiver circuitry (not shown) within the pacemaker. The pacemaker acknowledges reception of the telemetry request signal by generating an ACCEPT code consisting of an eight-bit word having alternating ones and zeros (10101010), and by serially supplying eight corresponding pairs of complementary signals to the telemetry system via the DDZER and DDONE lines. More specifically, with the ANENA line held low at this time to disable the analog telemetry circuitry and with at least one of the ANONE and ANTWO lines also held low, the DDONE line is set high while the DDZER line is held low. The high state on the DDONE line causes the reset (R) input of flip-flop 62 to go low through NOR gate 72, thereby enabling the frequency divider to generate complementary 10 kHz clock signals, and also causes a reset of counter 60 through gates 72 and 74, and thereby initiates generation of a digital data telemetry bit. Combinational logic 66 responds to the current states on the ANENA, DDZER and DDONE lines by gating only the A1 and Q5 output pulses through to AND gate 68, which is thus enabled during the intervals of those two pulses to gate the 10 kHz clock signal from D flip-flop 64 to one-shot 70 to form the sync pulse and digital data "1" pulse for the first telemetry bit.

Counter 60 is driven by the opposite phase of the 10 kHz clock, and its outputs sequentially go high for 100 μS each. The output pulses from AND gate 68 are only 50 μS in duration, however, due to the 50 μS duration of the high state of the 10 kHz clock, and are spaced in increments of 100 μS. Gate 68 thereby produces clock pulses for the first stage of one-shot 70 even in cases where the output of combinational logic 66 could otherwise remain high during the transition between desired pulses, such as when the Q2 output of counter 60 is gated through as required for generation of an analog channel ID pulse. Each output pulse from gate 68 enables the output stage of digital one-shot 70 to go high in response to the next positive-going transition of the 40 kHz main clock signal. Once the second stage goes high, it resets the first stage and thereby limits the duration of the output pulse on line 52 to one cycle of the 40 kHz clock, i.e., 25 μS. Thus, the first telemetry bit for the ACCEPT code consists of a sync pulse and a digital data pulse with their leading edges separated in time by 400 μS and each lasting 25 μS, thereby representing a digital data "1".

The second bit of the ACCEPT code is formed in a similar manner, but with DDZER high while DDONE is low. In this case, pulse generator 38 generates a sync pulse and a second pulse 200 μS thereafter, thereby representing a digital data "0". Six telemetry bits follow in the same 1-0 pattern to form a complete eight-bit ACCEPT code, and then, after a short delay during which the microprocessor may perform pacing or other functions, the telemetry mode is set via the telemetry control lines in accordance with the telemetry request.

If the requested telemetry mode is single-channel digital data only, ANENA, ANONE and ANTWO are all held low, and either DDZER or DDONE is set high depending on the state of the digital data bit which is desired to be transmitted during the next bit cycle. In the preferred format for digital data telemetry, eight consecutive bits representing the digital data are transmitted and immediately followed by a second eight consecutive bits representing the complement of the transmitted digital data.

For telemetry of purely analog data, DDZER and DDONE are both held low, ANENA is set high to enable analog telemetry, and one or the other of the analog telemetry channels is selected via the ANONE or ANTWO control lines. If single-channel analog telemetry is desired, ANONE is held high, whereas, if dual-channel analog telemetry is desired, one or the other of the ANONE or ANTWO control lines is momentarily pulled high during initialization to establish the initial state of flip-flop 78 and thereby determine which analog channel will operate first. The selected control line is preferably held high at least until the beginning of the BPREF pulse, and then ANONE and ANTWO are both held low, whereby channel selection flip-flop 78 toggles in response to the BPREF pulse for each subsequent telemetry bit. The pacemaker microprocessor is programmed to hold the ANENA line high as long as a reed switch (not shown) connected thereto in a conventional manner indicates the presence of the pacemaker programmer in close proximity. The system may alternatively be designed to transmit for predetermined periods of time in response to particular telemetry requests. In either event, the automatic cut-off of power to the analog telemetry circuit assists in avoiding premature battery drain.

The pacemaker microprocessor is also programmed to pause for at least 2 milliseconds between telemetry data words during digital data telemetry. As will be explained, such a pause or delay has the advantage of providing sufficient time for auto-synchronization of analog data if necessary, thereby limiting the amount of time the system can be out of sync without detection and correction to approximately the length of a digital data telemetry word.

Figure 7:
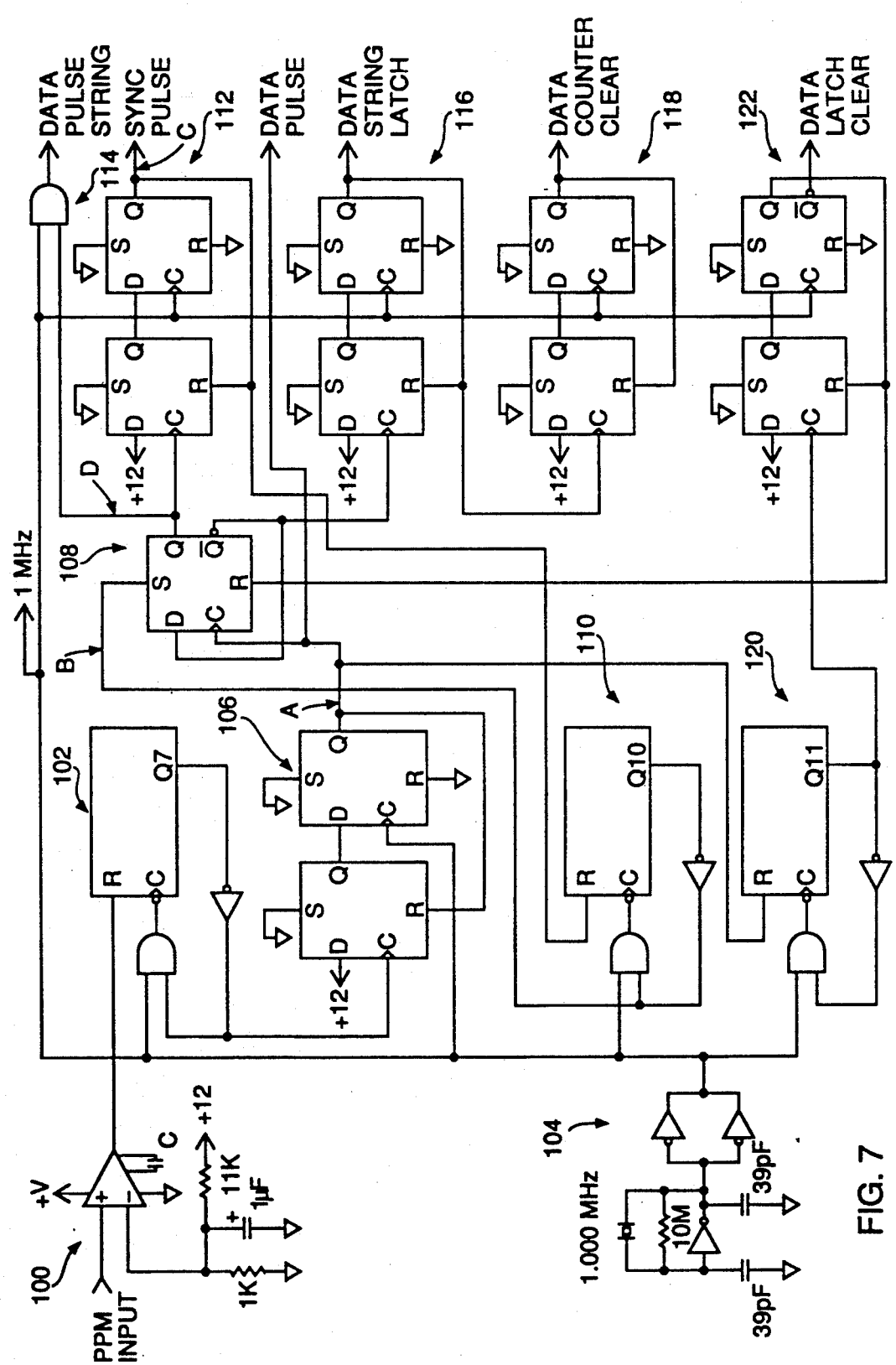
FIGS. 7-10 are electrical schematics of a telemetry receiver according to the preferred embodiment of the present invention.

Referring now to FIG. 7, the output of the telemetry transmitter is coupled from internal coupling coil 26 to a corresponding external coupling coil (not shown) in the associated receiver, which amplifies the signal received on the external coupling coil and supplies the amplified PPM signal to the PPM input shown in the drawing. A conventional analog input amplifier may be used to provide the desired amplification, which is preferably adjustable within a range of 80-100 db. The analog input amplifier is preferably configured as a bandpass filter with a center frequency of 100 kHz and −3 db points of 50 and 150 kHz. The PPM input of the receiver is connected to a comparator 100 designed around a CA3130 comparator IC and including the passive components illustrated in FIG. 7. The output of comparator 100 is supplied to the reset input of an input conditioning timer 102 built around a 4040 CMOS counter and configured so as to take 64 $\mu$S to time out in response to clock pulses from a 1 MHz clock 104. Timer 102 acts as a noise filter by rejecting input pulses which are separated by less than 64 $\mu$S. The pulses in any valid telemetry bit are separated by approximately 75 $\mu$S or more and are therefore passed in sequence to a digital one-shot 106 which generates a 1 $\mu$S output pulse in response to each incoming pulse from timer 102. Thus, for each transmitted pulse of the type shown in FIG. 3, a corresponding pulse is generated at point A in the circuit of FIG. 7 and supplied on the DATA PULSE line to the digital data demodulator illustrated in FIG. 10.

Each output pulse from one-shot 106 is also coupled to a data envelope latch 108, which toggles in response to each sync pulse and analog data pulse when the receiver is in sync with the transmitter. The resulting output signal at point D in the circuit represents the data envelope for the analog data. The data envelope is used as an enabling signal for an AND gate 114 which consequently passes 1 MHz clock pulses as a data pulse string for the duration of the data envelope. The data envelope duration is then measured by counting the clock pulses in the data pulse string, as will be described shortly.

Data envelope latch 108 also operates in conjunction with a phase restoration timer 110 and another one-shot 112 as a sync separator. Latch 108 is disabled for 512 $\mu$S after each sync pulse by phase restoration timer 110 which, like timer 102, is designed around a 4040 counter and receives its clock signal from 1 MHz clock 104. Timer 110 has an output connected to the set (S) input of latch 108, as shown in FIG. 7 (point B), and thereby holds the Q output of that latch high until timer 110 times out. Timer 110 is triggered by each output pulse from digital one-slot 112, which in turn is triggered by the positive-going edge of the data envelope produced by latch 108. Thus, when the telemetry transmitter and receiver are in sync in any mode which includes analog telemetry, the Q output of latch 108 goes high at the beginning of each sync pulse, and 1 $\mu$S later the Q output of the second stage of one-shot 112 goes high and thereby resets timer 110, which then holds the Q output of latch 108 high until all pulses in the current telemetry bit other than the analog data pulse have passed. The resulting output at point C in the circuit is the recovered string of sync pulses.

The circuitry of FIG. 7 also generates DATA STRING LATCH, DATA COUNTER CLEAR control pulses which, as will be described, are used in the demodulation of analog data. One-shot 116 generates a pulse on the DATA STRING LATCH line 1 $\mu$S after the end of the data envelope, in response to a clock pulse from latch 108 to which it is connected as shown in FIG. 7. The DATA COUNTER CLEAR control pulse is generated 1 $\mu$S after the DATA STRING LATCH control pulse by one-shot 118 which, as shown in the drawing, has its first-stage clock input connected to the output of one-shot 116 and which is driven by the same 1 MHz clock.

The circuit of FIG. 7 also includes an inactivity timer 120, also built around a 4040 counter, which is designed to produce a low output at the Q11 output of the counter as long as data pulses are regularly received during telemetry, but to time out and thereby produce a high output at Q11 in the absence of pulses for slightly longer than the expected interval between sync pulses, as an indication of the end of or a pause in telemetry. More specifically, the timer is designed to time out 1.024 milliseconds after it is triggered, i.e., 24 $\mu$S after the sync pulse for the next bit should arrive. One shot 122 generates a DATA LATCH CLEAR control signal whenever timer 120 times out, in order to clear the data latches in the event of detected inactivity. One-shot 122 also generates a pulse which resets data envelope latch 108 in such a case.

Figure 8:
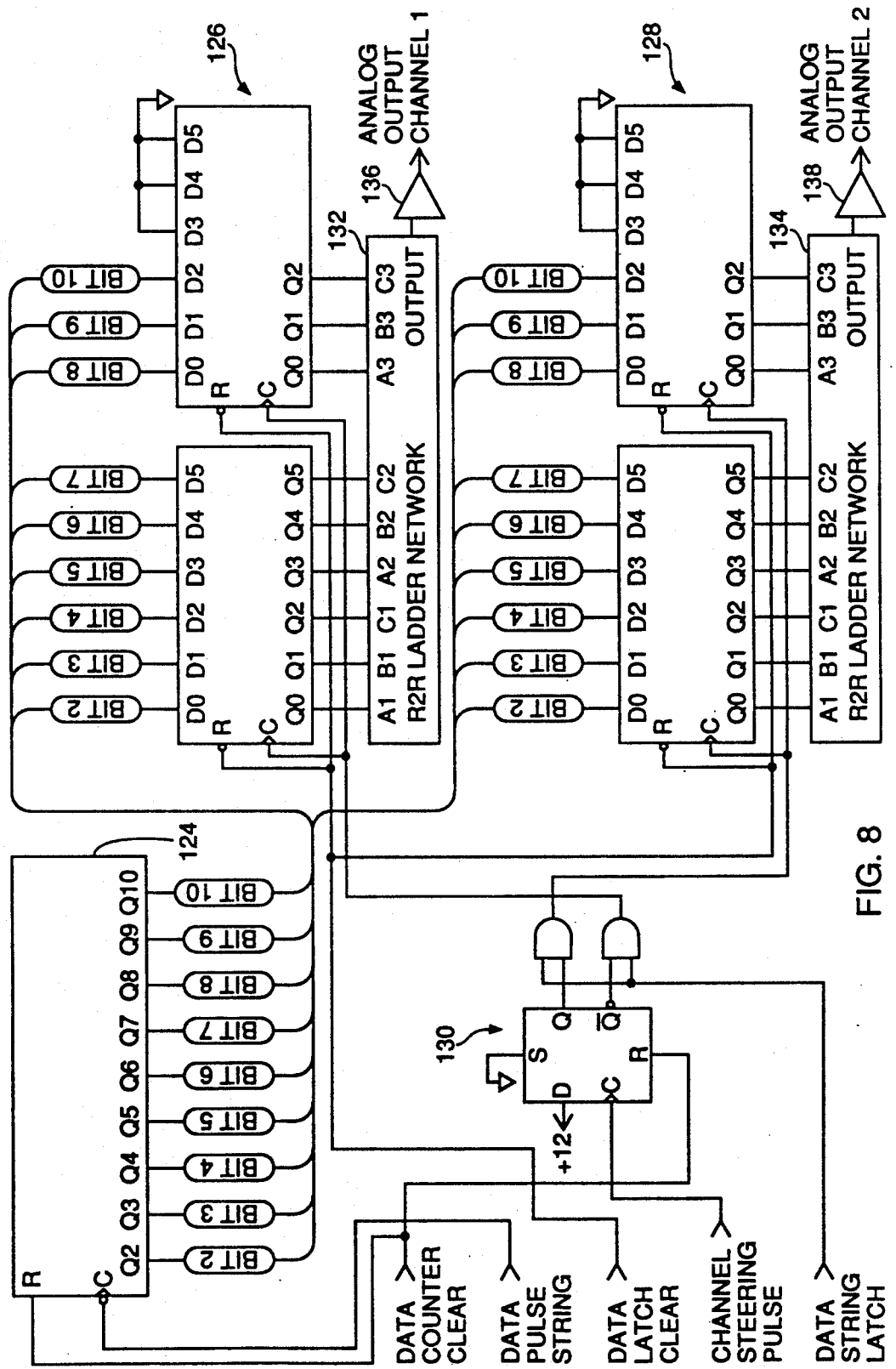

FIG. 8 illustrates the details of the analog demodulator circuitry, partly in schematic form and partly in block diagram form. The data pulse string from AND gate 114 is coupled to the clock input of data counter 124, another 4040 counter which, as shown in the drawing, has its Q2-Q10 outputs connected as bits 2-10 to the data inputs of latch circuits 126 and 128, each using a pair of 4174 latches as shown. This results in a resolution of 2 $\mu$S and, consequently, a count in the range of 300-400 for analog signals of interest.

Figure 9:
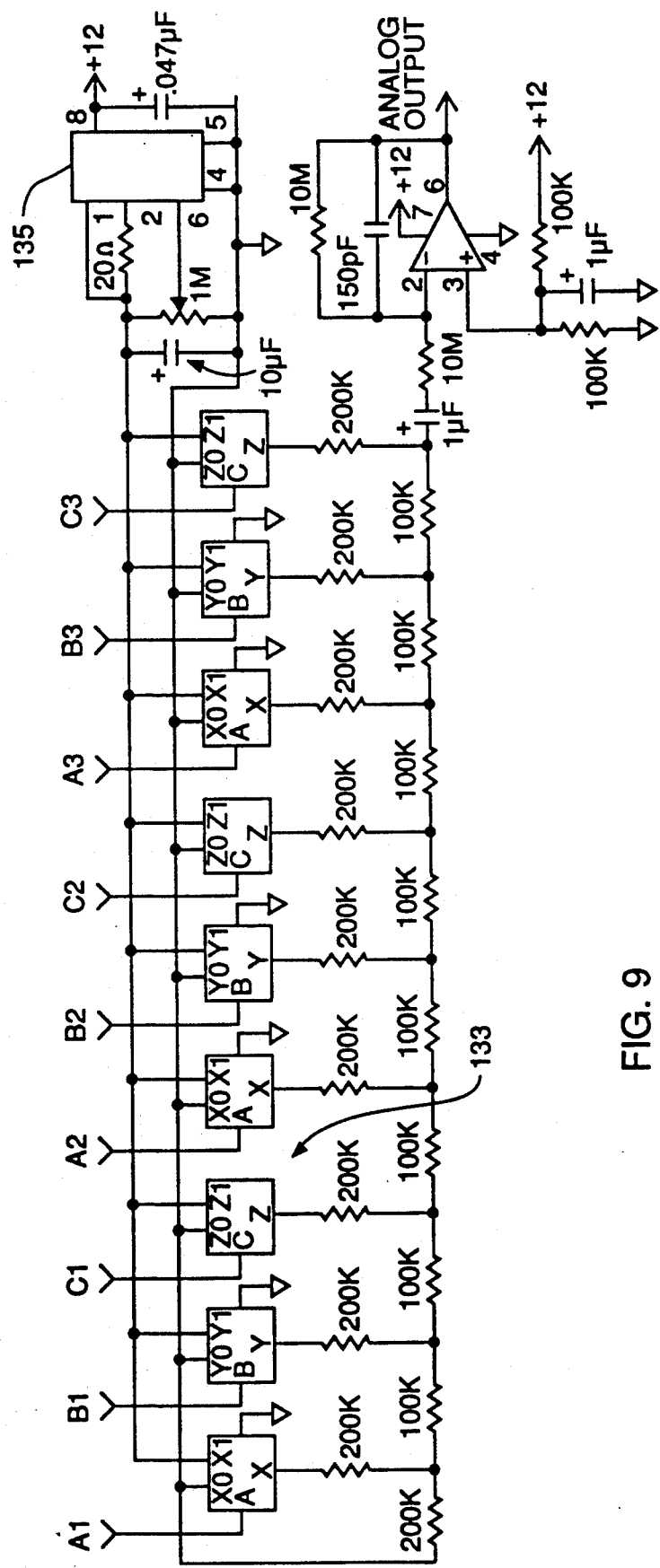

Latch circuits 126 and 128 have their reset inputs connected to the DATA LATCH CLEAR line described above with reference to FIG. 7, and have their clock inputs connected to respective AND gates in a multiplexer 130 which includes a D flip-flop with its complementary outputs arranged to enable one of the AND gates and disable the other. The DATA STRING LATCH pulse is thus steered to the appropriate latch circuit for the current analog data bit, in accordance with the channel steering pulse, which sets the flip-flop to steer the data to channel 2 when it is present. The flip-flop in MUX 130 is reset by the DATA COUNTER CLEAR pulse and thereby reverts after each latch pulse to its default state in which it steers analog data to channel 1. The current digital values in the latch circuits are converted to analog values by respective R-2R ladder networks 132 and 134 and associated bandpass amplifiers 136 and 138. Each ladder network and bandpass amplifier is as shown in FIG. 9, and preferably includes three 4053 analog multiplexers/demultiplexers 133 each configured as a digitally controlled 3PDT switch as shown in the drawing. The voltage reference for the ladder network is preferably provided by a Harris ICL7663 voltage regulator 135 and accompanying circuitry as shown in FIG. 9. Each bandpass amplifier is as shown in the drawing and preferably uses a CA3160 op amp.

The telemetry receiver has the capability of restoring correct analog phase in the event that a sync pulse is missing or incorrectly received for any reason. Phase restoration, or auto-synchronization, occurs during telemetry of analog data only, and will be explained with reference to the timing diagram of FIG. 11, which illustrates the waveforms found at the aforementioned points A, B, C and D in the circuit of FIG. 7 in response to two conditions to be described with reference to the illustrated four consecutive telemetry bits. The first and second bits illustrate the first condition, in which the sync pulse for a particular data bit is not received. A 180° phase inversion occurs as a result of the missing sync pulse because the analog data pulse, rather than the sync pulse, toggles data envelope latch 108 to begin the data envelope. In such a case, the data envelope extends until the beginning of the analog data pulse in the second bit because latch 108 is inhibited from changing state until after the sync pulse for the second bit arrives, as illustrated by the comparative waveforms at points A and B. Since no other pulse occurs before the next analog data pulse when only analog information is being transmitted, inhibiting latch 108 in this manner ensures that, if one analog data pulse does not terminate the data envelope, the next one will, assuming it is received. Thus, if the data envelope starts incorrectly with an analog data pulse rather than a sync pulse, as in the first bit of FIG. 11, the phase restoration timer enables the data pulse in the second bit to clock the data envelope latch low and thereby restore the correct phase. At this point the transmitter and receiver are in sync. The third bit and all following bits will be demodulated properly, as illustrated in FIG. 11, in which the third and fourth bits represent the normal condition in which a sync pulse is received first as desired.

One bit of information is lost in addition to any bit missing its sync pulse, but only two bits of information are lost as long as the system is transmitting analog data only. In the case of combined analog and digital telemetry, the system resynchronizes, if necessary, in the interval between digital data telemetry words, and thereby limits the loss of analog information to an interval less than 20 mS in the worst case, which is inconsequential during a real-time, analog data transmission which typically lasts at least 10 seconds and often extends for several minutes. For this reason, in the case of analog telemetry only, the operator of the receiver is not alerted to an analog telemetry error. An error message is displayed in response to detection of an error in digital data telemetry, and loss of a sync pulse would produce such an error, as will be described.

Figure 10:
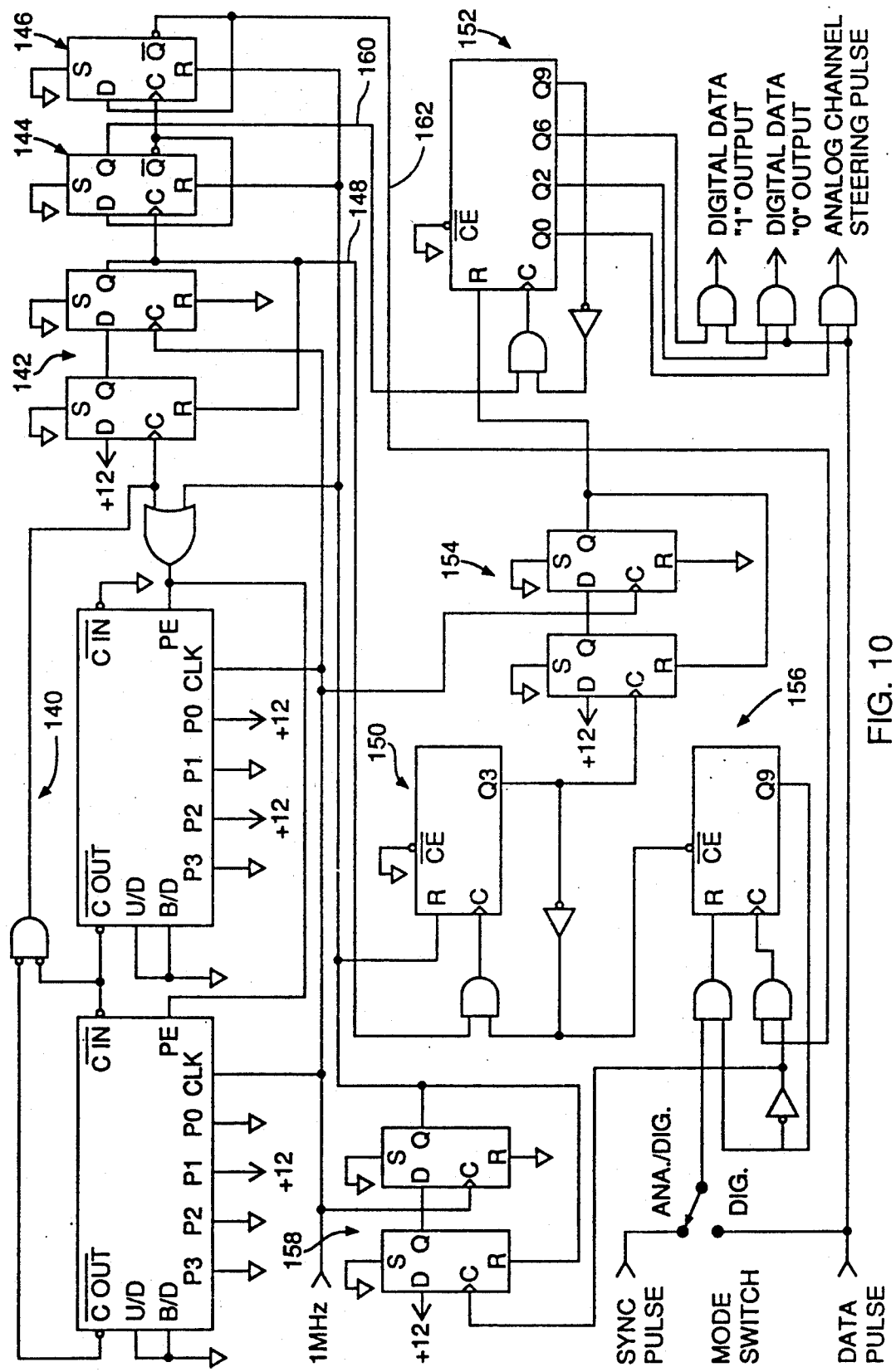

Turning now to FIG. 10, the 1 MHz clock signal generated by clock 104 is supplied to a divide-by-25 frequency divider 140 the output pulses from which are shaped by one-shot 142 and then supplied to a divide-by-2 frequency divider 144 which in turn is coupled to a second divide-by-2 frequency divider 146. Frequency divider 140 preferably uses two 4029 programmable counters, one 4001-type NOR gate and one 4071-type OR gate. 4013-type D flip-flops are suitable for one-shot 142 and dividers 144 and 146, as well as for one-shots 154 and 158 to be described. One-shot 142 supplies a clock pulse on output line 148 to a 75 $\mu$S delay timer 150, one output of which (Q3) is coupled to a "decoding-window" timer 152 through a pulse-forming one-shot 154. Delay timer 150 is triggered by yet another timer, a "total bit cycle" timer 156, through another pulse-forming one-shot 158, as illustrated in the drawing. All three timers just described are built aronud 4017 counters and use 4081-type AND gates and 4584-type inverters.

The digital data demodulator shown in FIG. 10 is designed to generate a series of decoding windows at predetermined times following reception of a sync pulse. Bit cycle timer 156 receives sync pulse either on the SYNC PULSE line from one-shot 112 in FIG. 7, to which it is connected through the mode switch shown in FIG. 10 during combined analog and digital data telemetry, or from the DATA PULSE line from one-shot 106 in FIG. 7, to which it is connected during telemetry of digital data only. In normal operation, a sync pulse from either source triggers the cycle timer, resetting its Q9 output, which is designed to be high at that time, and thereby triggers one-shot 158 which in turn triggers delay timer 150. The Q3 output of timer 150 goes low in response, and thereby disables cycle timer 156 via its clock enable input until delay timer 150 times out. Once triggered, delay timer 150 receives clock pulses on line 148 at the rate of one clock pulse every 25 $\mu$S, and, accordingly, times out in 75 $\mu$S. The resulting positive-going transition of the Q3 output signal causes one-shot 154 to generate a pulse which triggers decoding window timer 152, which is designed to have its Q9 output high and all other outputs low at this time. Timer 152 thereupon receives a clock pulse 50 $\mu$S from one-shot 144 along line 160, in response to which the timer outputs go high for 50 $\mu$S in sequence.

The combined effect of the 75 $\mu$S delay introduced by timer 150 and the series of 50 $\mu$S pulses generated by timer 152 at its Q0, Q2 and Q6 outputs, as shown, is a set of three windows, each 50 $\mu$S wide, centered at 100 $\mu$S, 200 $\mu$S and 400 $\mu$S after the leading edge of the sync pulse, respectively. The first window corresponds to the analog channel steering pulse, the second to the digital data "0" pulse, and the third to the digital data "1" pulse. With the DATA PULSE line connected to all three AND gates of window timer 152 as shown, any data pulse occurring during its respective time window results in a pulse appearing at its respective AND gate output. The three outputs of the digital data demodulator are periodically read by a microprocessor (not shown) within the receiver, and processed in a manner to be described.

Cycle timer 156, which receives clock pulses on line 162 from one-shot 146, is designed to take 975 $\mu$S to time out. Its timing cycle is initially delayed by 75 $\mu$S by delay timer 150, as explained above, and it takes 900 $\mu$S to time out once it begins counting, for a total of 975 μS, which is selected so as to leave minimal time prior to the expected reception of the next sync pulse. Timer 156 thereby inhibits inadvertent triggering of decoding window timer 152 which might otherwise result from pulses supplied through the mode switch.

The mode switch enables selection of the source of sync pulses for cycle timer 156. The mode switch is set to the digital (DIG) position when only digital information is to be transmitted, and is set to the analog and digital (ANA/DIG) position when combined analog and digital telemetry is desired. The sync separator described with reference to FIG. 7 is designed to separate the sync pulse from other telemetry pulses when analog data are transmitted, in that it relies on an analog data pulse to terminate the data envelope and thereby enable initiation of a new data envelope in response to the next sync pulse. In the absence of an analog data bit, as in digital-only mode, the data envelope does not terminate until the next sync pulse, and a new data envelope does not begin until the occurrence of the next digital data bit, resulting in the generation of a false sync pulse on the SYNC PULSE line at that time. Therefore, the sync separator is bypassed during digital-only mode in order to avoid loss of synchronization for digital data demodulation. During combined analog and digital telemetry, however, the sync separator performs as intended and is preferred as the source of sync pulses for the digital data demodulator because it minimizes the number of pulses supplied to the digital data demodulator and thereby minimizes the risk of false triggering. More specifically, as will be described, it is desirable to ensure a long gap after any false sync pulse occurring before cycle timer 156 times out, in order to detect a loss of synchronization by detecting absence of a digital data bit when expected.

The microprocessor in the receiver is programmed to check digital data for errors, as will now be described. The digital data "0" and "1" outputs of decoding window timer 152 are both read periodically by the microprocessor and decoded as follows:

| "0" Output | "1" Output | Decoded Data Value |
| --- | --- | --- |
| 0 | 0 | Invalid Code |
| 0 | 1 | 1 |
| 1 | 0 | 0 |
| 1 | 1 | Invalid Code |

The decoding window timer outputs are first checked for a valid code, which is indicative of data bit presence, and, in each case where a valid code is detected, the decoded digital value is temporarily stored for further checking. Once the presence of a first digital data bit is detected on the basis of a valid data code, the microprocessor checks successive outputs of the decoding window timer until it detects the expected number of digital data bits for the current telemetry mode or detects an invalid data code, whichever occurs first. The first digital data word expected by the receiver is the ACCEPT code, which, as described earlier, is 10101010. The receiver is also programmed to request and receive telemetry of event markers, which in the preferred embodiment are two-bit data words corresponding to four combinations of event markers which are desired in the pacemaker. The receiver is programmed to receive other digital data in the form of sixteen-bit telemetry data words, the first eight bits of which are the eight-bit data word being transmitted, and the second eight bits of which are the complement of the eight-bit data word, as mentioned earlier. If desired, an alternative format may be used in which the telemetry data word alternates on a bit-by-bit basis between a data bit and its complement, i.e., each bit in the eight-bit data word is followed immediately by its complement rather than by the next data bit.

It is adequate for many applications to multiplex analog and digital data only when it is desired to send marker signals along with analog data. However, the system is useful for multiplexing any form of digital data with analog data, and at any time within limits as required for correction of loss of synchronization. For example, it would be advantageous in some applications to transmit certain ones or all of the operating parameters of a pacemaker on a periodic basis any time telemetry is requested.

Invalid data codes occur before telemetry of digital data begins, and invalid codes can also result from loss of synchronization in some circumstances, for example, when a sync pulse is not received during transmission of digital data only. In this circumstance, cycle timer 156 is triggered by the next pulse received, which is the digital data pulse itself unless it too is missing. The data pulse thus results in a false sync pulse. Whether that data pulse is a 1 or a 0, neither one of the outputs of window timer 152 will go high during the ensuing telemetry data bit, because no pulse will appear on the DATA PULSE line within the windows provided for digital data at 200 μS and 400 μS after triggering of cycle timer 156. The receiver responds to detection of invalid data codes in this and other circumstances by generating an error signal or message which is displayed on a suitable display (not shown). Of course, window timer 152 also produces an invalid data code if the sync pulse is received but the data pulse is missing for any reason, and the response in this case also is an error message.

The receiver also generates an error message if the first data word received after a telemetry request does not match the 1-0 pattern of the ACCEPT code. For digital information transmitted in the sixteen-bit format described earlier, the telemetry receiver compares the first eight bits in the telemetry data word with the second eight bits and accepts the data as valid only if the second eight are the complement of the first eight as expected.

The error-checking routine programmed into the receiver microprocessor also detects loss of sync on the basis of invalid data codes resulting from a premature false sync pulse, that is, a pulse which is falsely detected as a sync pulse but which arrives before cycle timer 156 times out and is therefore too early to trigger a set of decoding windows for one telemetry bit. For example, if a digital data "1" is transmitted but the sync pulse is not received, the decoding windows for the telemetry bit are established with respect to the data pulse itself, which, as noted earlier, automatically results in an invalid data code in the absence of analog data. However, if single-channel analog data, for example, is combined with the digital data, and the analog data pulse for the out-of-sync telemetry data bit should happen to be positioned at either 600 μS or 800 μS after its associated sync pulse, the analog data pulse will be misinterpreted as a "0" or a "1", respectively. In such a case the receiver remains out of sync with the transmitter for the next telemetry bit because phase restoration timer 110 inhibits clocking of envelope latch 108 until after the analog data pulse, and the next sync pulse therefore clocks latch 108 low rather than high as it should to generate a sync pulse for the digital data demodulator at the proper time. As a result, another false sync pulse is generated in response to the next digital data pulse. If that next data pulse is also a 1, the error continues undetected. However, if the next data pulse is a 0, as it would be, at the latest, when the data complement is transmitted, the "0" pulse causes a false sync pulse to be generated 800 µS after the last false sync pulse and therefore too early to retrigger cycle timer 156 for generation of a set of decoding windows for the new telemetry bit. As a result, both data outputs of the window timer are low when read by the microprocessor, which responds by generating an error message.

Loss of synchronization can also be detected during the complement check in certain situations, e.g., where the receiver synchronizes on the analog data pulse of a telemetry bit for which the sync pulse and digital data pulse are somehow lost during transmission. Such a situation would normally be recognized immediately by an invalid data code resulting from absence of digital data within the defined decoding windows, which in this case would follow the analog data pulse. However, if the receiver synchronizes on an analog data pulse positioned at 600 µS after its associated sync pulse for the next bit is misinterpreted by the receiver as a digital data "1" because it falls within the window centered at 400 µS after the (false) sync pulse. The actual digital data pulse for that next bit terminates the data envelope and thereby enables generation of another false sync pulse in response to the next analog data pulse. Therefore, the demodulator output remains a "1" as long as the analog data pulse remains at the 600 µS position. If not detected sooner due to a change in analog value, the error is detected during the complement check, because the resulting decoded telemetry data word will be sixteen ones, which cannot occur with any valid data with the telemetry data format used in the described system.

In the alternative telemetry data format described above, in which each digital data bit is followed immediately by its complement, the likelihood of undetected error is even further reduced because the format ensures that a "0" will follow a "1" sometime during the telemetry data word, such that, if the sync separator somehow misidentifies a digital data "1" as the sync pulse, a premature false sync pulse will appear at some point thereafter during reception of the telemetry data word, either in response to a "0" pulse or, in the case of digital telemetry combined with dual-channel analog telemetry, in response to an analog channel ID pulse. This alternative format can also increase the problem of error detection in other situations, including erroneous synchronization on analog data pulses.

In another alternative embodiment, the analog channel steering pulse output of window timer 152 is checked in the error-checking routine during dual-channel analog telemetry mode. If the steering pulse does not appear as expected in alternate telemetry data bits, the microprocessor generates an error message. Also, if desired, errors in analog telemetry may be detected by monitoring the SYNC PULSE line and generating an error message if the time between expected sync pulses exceeds 1 mS by a predetermined amount.

Although described above as an electrical switch, the mode switch in the digital data demodulator may alternatively be an electronic switch controlled by the receiver microprocessor automatically in response to mode selections made via a keyboard provided for control of the receiver and a pacemaker programmer which is preferably included with the receiver. It is further contemplated that many of the digital processing functions described in connection with the receiver, such as input conditioning, phase restoration, inactivity detection, delay and other timing functions, control signal generation, and clock frequency division, may be provided in software within the receiver microprocessor along with the above-described error-checking routines.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A synchronous telemetry system for a pacemaker, comprising:
   means for generating a plurality of telemetry sync pulses;
   an analog signal input;
   pulse-position modulation means for generating an analog data pulse after each of said sync pulses and equal thereto in amplitude, said pulse-position modulation means including means for displacing each analog data pulse from its respective sync pulse by a time interval corresponding to the instantaneous value of an analog signal at said analog signal input; and
   means for transmitting said sync pulses and said analog data pulses from said pacemaker to an external device.

2. The synchronous telemetry system of claim 1 wherein said pulse-position modulation means includes means for generating each said analog data pulse within a predetermined time window following its respective sync pulse by a predetermined minimum time interval.

3. The synchronous telemetry system of claim 2, further comprising a digital signal input,
   wherein said pulse-position modulation means further includes means for generating a digital data pulse within each of said predetermined minimum time intervals and displaced from its respective sync pulse by a discrete interval corresponding to the instantaneous state of a digital signal at said digital signal input; and
   wherein said transmitting means includes means for transmitting said digital data pulses along with said sync pulses and said analog data pulses.

4. The synchronous telemetry system of claim 3 wherein said pulse-position modulation means further includes a voltage-controlled variable one-shot having a trigger input connected to said sync pulse generating means and having a pulse interval control input connected to said analog signal input.

5. A synchronous telemetry system for a pacemaker, comprising:
   means for generating a plurality of telemetry sync pulses;
   an analog signal input;
   pulse-position modulation means for generating an analog data pulse after each of said sync pulses and equal thereto in amplitude, said pulse-position modulation means including means for displacing each analog data pulse from its respective sync pulse by a time interval corresponding to the instantaneous value of an analog signal at said analog signal input; and means for transmitting said sync pulses and said analog data means from said pacemaker to an external device;

wherein said pulse-position modulation means includes means for generating each said analog data pulse within a predetermined time window following its respective sync pulse by a predetermined minimum time interval; and further comprising means for multiplexing analog data pulses within said predetermined time window, and means for indicating the source of an analog data pulse within said time window with an identification pulse outside said time window.

6. A synchronous telemetry method for a pacemaker, comprising the steps:

generating a plurality of telemetry sync pulses;

generating an analog data pulse after each of said sync pulses and equal thereto in amplitude, said generating step including displacing each analog data pulse from its respective sync pulse by a time interval corresponding to the instantaneous value of an analog input signal; and transmitting said sync pulses and said analog data pulses from said pacemaker to an external device.

7. The synchronous telemetry method of claim 6 wherein said data-pulse-generating step includes generating each said analog data pulse within a predetermined time window following its respective sync pulse by a predetermined minimum time interval.

8. The synchronous telemetry method of claim 7, further comprising the step of generating a digital data pulse within each of said predetermined minimum time intervals and displaced from its respective sync pulse by a discrete interval corresponding to the instantaneous state of a digital input signal, wherein said transmitting step includes transmitting said digital data pulses along with said sync pulses and said analog data pulses.

9. A synchronous telemetry method for a pacemaker, comprising the steps:

generating a plurality of telemetry sync pulses;

generating an analog data pulse after each of said sync pulses and equal thereto in amplitude, said generating step including displacing each analog data pulse from its respective sync pulse by a time interval corresponding to the instantaneous value of an analog input signal; and transmitting said sync pulses and said analog data pulses from said pacemaker to an external device;

wherein said data-pulse-generating step includes generating each said analog data pulse within a predetermined time window following its respective sync pulse by a predetermined minimum time interval; and further comprising the steps of multiplexing analog data pulses within said predetermined time window, and indicating the source of an analog data pulse within said time window with an identification pulse outside said time window.

10. A synchronous telemetry system for multiplexed telemetry of analog and digital information from an implantable medical device, comprising:

means for generating a plurality of telemetry sync pulses;

an analog signal input;

a digital signal input;

pulse-position modulation means for generating an analog data pulse and a digital data pulse for each sync pulse and equal thereto in amplitude, said pulse-position modulation means including means for displacing each said analog data pulse and each said digital data pulse from their respective sync pulse by different time intervals respectively corresponding to the instantaneous value of an analog signal at said analog signal input and the instantaneous state of a digital signal at said digital signal input; and means for transmitting said sync pulses and said analog and digital data pulses to an external device.

11. The synchronous telemetry system of claim 10 wherein said pulse-position modulation means includes means for generating each said analog data pulse within a predetermined time window following its respective sync pulse by a predetermined minimum time interval.

12. The synchronous telemetry system of claim 11, wherein said pulse-position modulation means includes means for generating said digital data pulse within said predetermined minimum time interval.

13. A synchronous telemetry system for multiplexed telemetry of analog and digital information from an implantable medical device, comprising:

means for generating a plurality of telemetry sync pulses;

an analog signal input;

a digital signal input;

pulse-position modulation means for generating an analog data pulse and a digital data pulse for each sync pulse, said pulse-position modulation means including means for displacing each said analog data pulse and each said digital data pulse from their respective sync pulse by different time intervals respectively corresponding to the instantaneous value of an analog signal at said analog signal input and the instantaneous state of a digital signal at said digital signal input;

means for transmitting said sync pulses and said analog and digital data pulses to an external device;

wherein said pulse-position modulation means includes means for generating each said analog data pulse within a predetermined time window following its respective sync pulse by a predetermined minimum time interval;

wherein said pulse-position modulation means includes means for generating said digital data pulse within said predetermined minimum time interval; and further comprising multiplexer means for multiplexing signals from a plurality of analog channels coupled to said analog signal input, said multiplexer means including means for generating an analog data pulse within said predetermined time window for a signal from a selected one of said analog channels, and means for indicating the corresponding analog channel with a channel identification pulse outside said time window.

14. A synchronous telemetry method for multiplexed telemetry of analog and digital information from an implantable medical device, comprising the steps:

generating a plurality of telemetry sync pulses;

generating an analog data pulse and a digital data pulse for each sync pulse and equal thereto in amplitude, said data-pulse-generating step including displacing each said analog data pulse and each said digital data pulse from their respective sync pulse by different intervals respectively corresponding to the instantaneous value of an analog input signal and the instantaneous state of a digital input signal; and transmitting said sync pulses and said analog and digital data pulses to an external device.

15. The synchronous telemetry method of claim 14 wherein said data-pulse-generating step includes generating each said analog data pulse within a predetermined time window following said same sync pulse by a predetermined minimum time interval.

16. The synchronous telemetry method of claim 15, wherein said data-pulse-generating step includes generating said digital data pulse within said predetermined minimum time interval.

17. A synchronous telemetry method for multiplexed telemetry of analog and digital information from an implantable medical device, comprising the steps:

generating a plurality of telemetry sync pulses;

generating an analog data pulse and a digital data pulse for each sync pulse, said data-pulse-generating step including displacing each said analog data pulse and each said digital data pulse from their respective sync pulse by different intervals respectively corresponding to the instantaneous value of an analog input signal and the instantaneous state of a digital input signal;

transmitting said sync pulses and said analog and digital data pulses to an external device;

wherein said data-pulse-generating step includes generating each said analog data pulse within a predetermined time window following said same sync pulse by a predetermined minimum time interval;

wherein said data-pulse-generating step includes generating said digital data pulse within said predetermined minimum time interval; and further comprising the steps:

multiplexing signals from a plurality of analog channels coupled to said analog signal input, said multiplexing step including generating an analog data pulse within said predetermined time window for a signal from a selected one of said analog channels; and indicating the corresponding analog channel with a channel identification pulse outside said time window.

18. A synchronous telemetry system for a pacemaker, comprising:

means for generating a plurality of telemetry sync pulses;

an analog signal input;

pulse-position modulation means for generating an analog data pulse for each of said sync pulses, said pulse-position modulation means including means for displacing each analog data pulse from its respective sync pulse by a time interval corresponding to the instantaneous value of an analog signal at said analog signal input;

means for multiplexing analog data pulses within a predetermined time window following each sync pulse;

means for indicating the source of an analog data pulse within said time window with an identification pulse outside said time window; and means for transmitting said sync pulses, analog data pulses and identification pulses from said pacemaker to an external device.

19. The synchronous telemetry system of claim 18, further comprising a digital signal input, wherein said pulse-position modulation means further includes means for generating a digital data pulse outside said predetermined time window and displaced from its respective sync pulse by a discrete interval corresponding to the instantaneous state of a digital signal at said digital signal input; and wherein said transmitting means includes means for transmitting said digital data pulses along with said sync pulses, analog data pulses and identification pulses.

20. A synchronous telemetry method for a pacemaker, comprising the steps:

generating a plurality of telemetry sync pulses;

generating an analog data pulse for each of said sync pulses, said generating step including displacing each analog data pulse from its respective sync pulse by a time interval corresponding to the instantaneous value of an analog input signal;

multiplexing analog data pulses within a predetermined time window following each sync pulse;

indicating the source of an analog data pulse within said time window with an identification pulse outside said time window; and transmitting said sync pulses, analog data pulses and identification pulses from said pacemaker to an external device.

21. The synchronous telemetry method of claim 20, further comprising the step of generating a digital data pulse outside said predetermined time window and displaced from its respective sync pulse by a discrete interval corresponding to the instantaneous state of a digital input signal, wherein said transmitting step includes transmitting said digital data pulses along with said sync pulses, analog data pulses and identification pulses.

* * * * *

UNITED STATES PATENT AND TRADEMARK OFFICE
CERTIFICATE OF CORRECTION

PATENT NO. : 5,137,022

DATED : August 11, 1992

INVENTOR(S) : Donald A. Henry

It is certified that error appears in the above-identified patent and that said Letters Patent is hereby corrected as shown below:

In column 1, line 7, please change "The" to --This--.
In column 1, line 7, please change "telementry" to --telemetry--.
In column 1, line 8, please change "cardial" to --cardiac--.

In column 8, line 12, please change "Al" to --Q1--.
In column 10, line 9, please change "slot" to --shot--.
In column 10, line 44, please change "One shot" to --One-shot--.
In column 12, line 20, please change "aronud" to --around--.
In column 12, line 26, please change "pulse", second occurrence, to --pulses--.
In column 12, line 46, please insert --every-- after "pulse".
In column 15, line 26, please insert --,the sync pulse-- after "pulse".
In column 17, line 6, please change "means" to --pulses--.

Signed and Sealed this

Twenty-first Day of September, 1993

Attest:

BRUCE LEHMAN

Attesting Officer

Commissioner of Patents and Trademarks